(12) United States Patent
Hoftman

(10) Patent No.: US 9,750,891 B1
(45) Date of Patent: Sep. 5, 2017

(54) DEVICE FOR SAFE WITHDRAWAL AND ADMINISTRATION OF LIQUIDS BY SYRINGE

(76) Inventor: Moshe Mike Hoftman, Calabasas, CA (US)

( * ) Notice: Subject to any disclaimer, the term of this patent is extended or adjusted under 35 U.S.C. 154(b) by 0 days.

(21) Appl. No.: 12/938,054

(22) Filed: Nov. 2, 2010

Related U.S. Application Data

(60) Provisional application No. 61/281,468, filed on Nov. 17, 2009.

(51) Int. Cl.
*A61M 5/32* (2006.01)

(52) U.S. Cl.
CPC ........ *A61M 5/3202* (2013.01); *A61M 5/3213* (2013.01); *A61M 5/3216* (2013.01)

(58) Field of Classification Search
CPC . A61M 5/3202; A61M 5/3213; A61M 5/3216
USPC ... 604/192, 263, 198, 163, 164.08, 197, 533
See application file for complete search history.

(56) References Cited

U.S. PATENT DOCUMENTS

| 4,624,393 | A | * | 11/1986 | Lopez | 222/83.5 |
| 4,759,756 | A | * | 7/1988 | Forman | A61J 1/2089 604/413 |
| 4,932,944 | A | * | 6/1990 | Jagger | A61M 39/04 604/191 |
| 6,616,632 | B2 | | 9/2003 | Sharp et al. | |

* cited by examiner

*Primary Examiner* — Emily Schmidt
*Assistant Examiner* — Lauren M Peng

(57) ABSTRACT

The present invention provides a deflectable guide whose use results in protection of the hand of medical personnel holding a medical container during the activity of moving a hypodermic needle toward and pressing it through a septum of the medical container. The present invention further is adapted for use of the same syringe and deflector guide protected needle for injection or withdrawal of medical liquids from a septum end of medical catheter or intravenous tubing without removal of the deflectable guide.

12 Claims, 7 Drawing Sheets

DEVICE FOR SAFE WITHDRAWAL AND ADMINISTRATION OF LIQUIDS BY SYRINGE

This non-provisional application claims the benefit of priority under 35 U.S.C. 119(e) to U.S. Provisional Patent Application Ser. No. 61/281,468, filed Nov. 17, 2009, which is herein incorporated by reference in its entirety.

FIELD OF THE INVENTION

The present invention relates to withdrawal from septum vial or container and subsequent administration by hypodermic syringe of medically required liquids. More specifically, the invention relates to devices protecting medical personnel during such actions.

BACKGROUND OF THE INVENTION

Medical personnel are routinely required to inject and/or withdraw from medical containers, such as vials, bottles, and flexible bags, medically required liquids using a syringe engaged with a hypodermic needle or other septum puncturing means. Some of such medical containers have ready to use concentrates which must be withdrawn for injection into a larger volume of liquid in a separate medical container. Other such medical containers have ready to use liquids containing medication or flushing liquids to be administered directly to patients. Still other such medical containers have dry powders which must receive by injection a measured amount of liquid for reconstitution of a medical liquid to be used as a concentrate or ready to use liquid.

This activity of injection and withdrawal related to the above medical containers is deceptively simple. The time and emotional pressure typical of the medical treatment environment results in many improperly directed needle placements by medical personnel. A substantial focus of the prior art is made toward improving safety during the activity of hypodermic needle injection or withdrawal of fluids and liquids from a patient's veins, arteries, or other subcutaneous location. However, the present inventor has observed that doctors, nurses, pharmacists, and other healthcare professionals must, with one hand, hold such a medical container upside down and insert a hypodermic needle connected to a syringe through a rubber or elastomer septum of the medical container with the other hand, sometimes resulting in a needle puncture wound (sometimes quite deep) to the hand holding the medical container. Alternately, a needle puncture may occur to a medical tube conduit for intravenous fluids or to a flexible bag receiving injectable liquids from the syringe. The medical personnel administering or withdrawing liquids via syringe need only make a minor misalignment caused by lack of focus or an unsteady hand to cause such injury or damage.

It is well known that removal or covering of the hypodermic needle from the syringe upon completion of injection or withdrawal of medical liquids is most quickly and inexpensively achieved by re-inserting the hypodermic needle into a sheath from which it has been withdrawn originally, yet another maneuver which exposes medical personnel to needle sticks. This danger is so significant that OSHA has mandated that hypodermic needles should not be recapped in order to reduce the needle stick risk to the medical personnel.

The risks of accidental puncture wounds or misdirected punctures by hypodermic needles are well known in the art: The bodily fluids or tissues of the medical personnel wounded contaminate the needle exterior and internal bore toward the tip. The rushed, non-cognizant, or negligent medical personnel take further actions which result in their bodily fluids or tissues being injected into a patient or becoming a contaminant to bodily fluids withdrawn from a patient.

Medically significant quantities of medical liquids, some of which can be toxic, allergenic, or substantially radioactive, are injected into medical personnel, many times without actual knowledge of such personnel if the needle gauge is small and the puncture was swift.

Pathogens and bodily fluids located on the outside surface of protective gloves of medical personnel during a surgical or wound examination procedure may adhere to a hypodermic needle pressed through the glove and into the hand of the medical personnel holding the medical container.

It is common that one person will hold a medical container while another impresses a hypodermic needle into the septum, further increasing the risk of hypodermic needle puncture by way of a syringe holder not sensing proper alignment of the medical container.

Inherent dangers of injection and withdrawal of liquids from medical containers have resulted in development of "needleless" blunt-tipped plastic cannulas to replace sharp hypodermic needles. These cannulas have the advantage of being essentially far less capable puncturing human skin during typical medical procedures. However, blunt plastic cannulas are also inherently quite difficult to press into and through rubber septa, making loss or misalignment of the medical container a substantial risk. Dropping of a medical container during a needleless cannula piercing of a septum is a substantial risk and often renders the medical container contaminated beyond recovery, requiring instant disposal.

There is an immediate need for a device which is directed to essentially eliminating many of the risks of hypodermic needle puncture and/or misdirection of a hypodermic needle when pressed toward and through a rubber or elastomer septum of a medical container.

SUMMARY OF THE INVENTION

The present invention provides a deflectable guide whose use results in protection of the hand of medical personnel holding a medical container during the activity of moving a hypodermic needle toward and pressing it through a septum of the medical container. The present invention further is adapted for use of the same syringe and deflector guide protected needle for injection or withdrawal of medical liquids from a septum end of medical catheter or intravenous tubing without removal of the deflectable guide.

The invention deflectable guide has a plurality of arcuate sections oriented parallel to and spaced radially and uniformly from an operating axis defined by a bore of a hypodermic needle of a combination of said needle fixed to a tip of a syringe. Each arcuate section is fixed at an upper end by way of a radial spacing support to a top part of said needle or a lower part of the syringe.

When not in use as applied to medical containers, the arcuate sections of the invention deflectable guide are adapted to define a generally cylindrical or slightly frustroconical medical container space by their inwardly directed surfaces. In one form of the invention, one or more slots are defined between downward edges of adjacent arcuate sections. In another form of the invention, edges of adjacent arcuate sections overlap but slide easily over one another when required to be flexed outward to accomplish the objects of the invention.

The present invention of a deflectable guide is effective upon cylindrical medical containers, which are the primary form of medical containers. Further, in a form of the invention adapted for outward deflection, it is intended that the outside diameter of such cylindrical medical containers must be greater than an effective cylindrical inside diameter of the medical container space defined by inside, generally opposing surfaces of the arcuate sections.

Further, it is intended that, to avoid needle wounds for medical staff, the hypodermic needle must be shorter in length than an effective downward extension of the lower ends of the arcuate sections and the medical container space.

For a hypodermic needle and syringe combination equipped with the invention deflectable guide, it is a primary object of the invention that a user shall apply lower ends of the arcuate sections generally uniformly upon an upper (usually sloped or shouldered) part of a cylindrical medical container and thereafter impress the needle end into the septum of the medical container. Arcuate sections are adapted to flex outward from their lower ends, embracing and impressing their inside surfaces uniformly upon an upper end of the cylindrical form factor of the medical container. Said arcuate sections are sufficiently rigid in their connection to the needle and syringe combination that impression of the deflectable guide upon the medical container results in automatic correction of alignment of a tip of said needle toward the septum of the medical container.

It is a further object of the invention to provide a self-correcting deflectable guide for a user of needle and syringe combination such that a user's hand is protected by arcuate sections against needle wounds during impression of the needle into a septum of a medical container.

It is yet a further object of the invention to provide means for arcuate sections to be integrally fixed to a top end of said hypodermic needle by way of the radial spacer support. In one form of the invention, a polymer syringe tip adapter of the needle is molded integrally with the radial spacer support extending radially to a top end of a further integrally molded arcuate section. In this form of the invention, a user will apply the syringe adapter of hypodermic needle to the tip of the syringe holding a top part of the deflectable guide, generally about the radial spacer support. When the hypodermic needle is so integrally fixed by its polymer or metal syringe adapter to the radial spacer support of the deflectable guide, the operating axis of the hypodermic needle is necessarily also the central operating axis of the deflecting arcuate sections. Thus, it is a preferred embodiment of the invention that the deflectable guide be integral with the syringe tip adapter of the hypodermic needle to maximize effectiveness of the objects of the invention as to self-directing the tip of the hypodermic needle to a septum of a medical container.

It is yet a further object of the invention to provide means for arcuate sections to be fixed to a top end of said hypodermic needle by way of the radial spacer support by way of a connection formed after the hypodermic needle is fixed to a tip of the syringe. In this form of the invention, a user shall fix a hypodermic needle to a tip of a syringe and thereafter fix the deflectable guide to the syringe tip adapter. This connection may be made by way of threaded connection with threads on the outside of surface of the syringe tip adapter of the hypodermic needle and mating threads on an inside surface of a central bore of the radial spacer support, whereby a user may pass the slender metal needle part of the hypodermic needle through the central bore of the deflectable guide until mating threads meet and are joined. One advantage of a later connectable deflectable guide is that hypodermic needles need not be sterilized and packaged with the large diameter deflectable guide integrally attached to the needle. The deflectable guide itself may, in some cases need not be sterilized for a connectable form of the invention.

The invention medication drawing system where the deflectable guide is effectively connected with a hypodermic needle and syringe combination allows for easy medication drawing via a shielded hypodermic needle. This novel assembled device aligns medical container's rubber or elastomer septum the tip of the hypodermic needle and its operating axis. The assembled device enables easy medication drawing and shields the tip of the hypodermic needle upon removal of the needle from the medical container such that accidental needle sticks cannot occur. The invention assembled device also allows for safe medication injection into inlet tubing rubber or elastomer ports without the risk of needle-stick wounds.

A further object of the invention is to provide a flexible shield inwardly deflectable at lower ends of the arcuate sections by a user's hand to impress inside surfaces of the arcuate sections upon a medical container smaller in diameter than the cylindrical or frustro-conical container space. Upon relatively slight impression of the arcuate sections upon the smaller diameter medical container by a user's thumb and forefinger, the hypodermic needle and syringe combination is easily impressed downward so the needle tip pierces the septum of the medical container, thereby protecting the hand of the user.

A further object of the invention is to provide a flexible shield inwardly deflectable at lower ends of the arcuate sections by a user's hand to impress inside surfaces of the arcuate sections upon a medical container so much smaller in diameter than the cylindrical or frustro-conical container space that said inside surfaces do not effectively engage the medical container. Some medical containers are of such small diameter and overall height that the deflectable guide effectively contains them within its container space. The invention deflectable guide still protects the user's hand by shielding the user's hand and providing a general axial guide for the septum of the small medical containers.

It is in general an object of the invention to protect a user's hand bearing a cylindrical medical container from needle wounds during impression of the tip of a needle of a combination of a syringe and a hypodermic needle into a septum. The invention assembled device comprises a deflectable guide, a hypodermic needle and a syringe.

DETAILED DESCRIPTION OF THE INVENTION

The invention is now discussed with reference to the figures.

Figure 1:
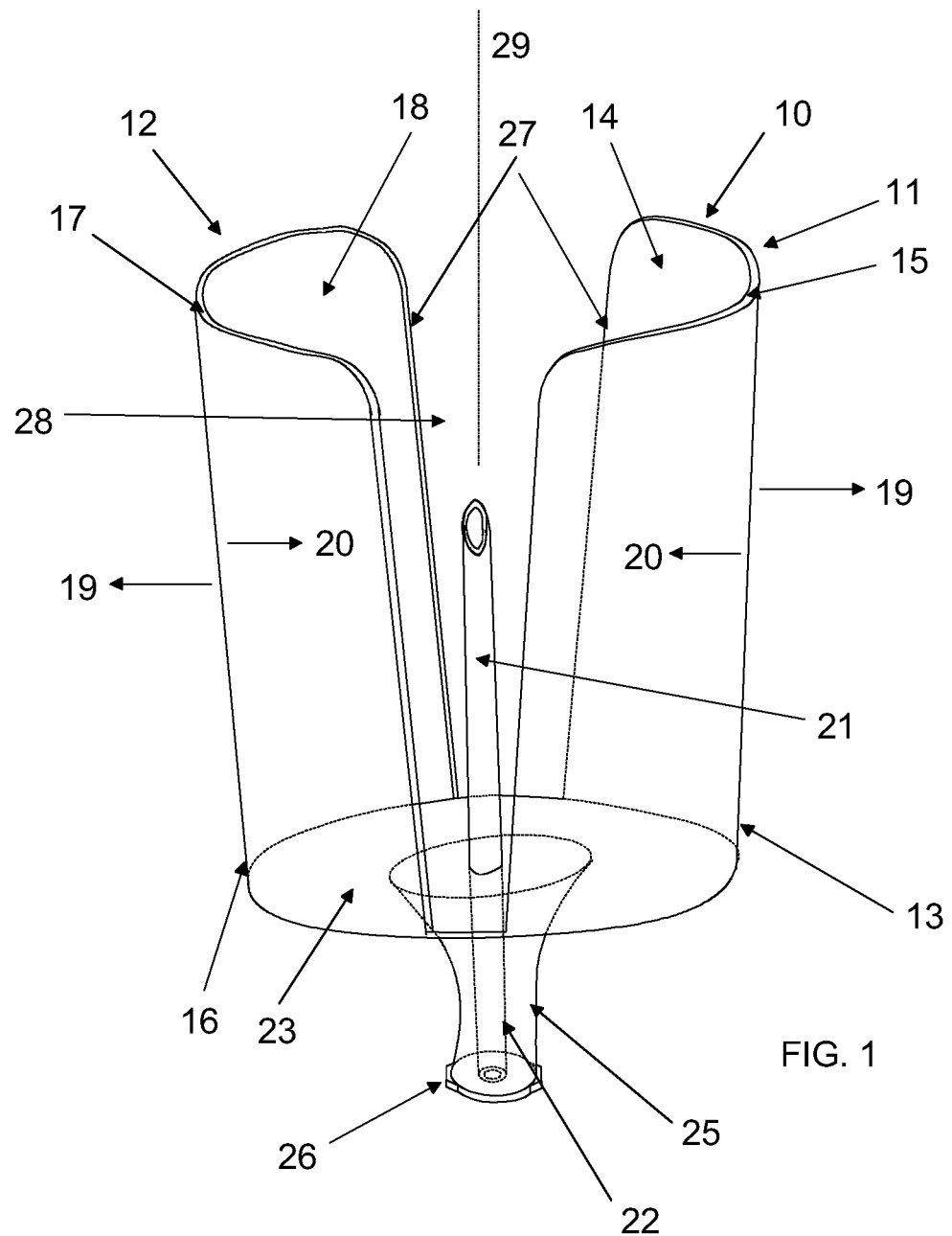
FIG. 1 is an upward, perspective view of the deflectable guide of an assembled device forming a medication drawing system.

FIG. 1 is an upward, perspective view of the deflectable guide 10 of an assembled device forming a medication drawing system. Generally, a syringe tip adapter 25 (with a Luer lock connector 26) extends laterally and radially from an operating axis 29, said axis 29 running the length of a bore of hypodermic needle 21 to form a radial spacer support 23, which rigidly connects arcuate sections 11 and 12 at upper ends 13 and 16 respectively to adapter 25. It will be appreciated that fixing adapter 25 to a syringe tip necessarily causes the sections 11 and 12 to be integrally fixed in orientation at their upper ends 13 and 16 with relation to said syringe as would be the case for needle 21. It is critical to the objects of the invention that such rigid connection of upper ends 13 and 16 be maintained with respect to their orientation to adapter 15, needle 21 (which is fixed in adapter 25 at portion 22), and a connected syringe. Sections 11 and 12 are deflectable outwardly in direction 19 or inward in direction 20, such that lower ends 15 and 17 experience maximum deflection and ends 13 and 16 experience minimum deflection. Sections 11 and 12 define two slots 28 by their opposing edges 27. These slots allow for deflection in directions 19 or 20 respectively of sections 11 and 12 as required for a user's interaction with a cylindrical medical liquids container. It will be appreciated that inside surfaces 14 and 18 are formed with a concave, arcuate shape to receive and embrace cylindrical medical liquid containers. Contact of a medical liquid container of greater outside diameter than the inside diameter between inside surfaces 14 and 18 first results in outwardly deflective contact between lower edges 15 and 17 and then with sliding upward contact with inside surfaces 14 and 18, thereby forcing lower ends or edges 15 and 17 even farther apart.

Deflectable guide 10 comprises a radial spacer support 23 with an effective inside diameter preferably of from a smallest outside diameter of a smallest septum top (about 0.5 inches) to about 2.0 inches, with operating axis lengths of from 0.5 inches to 3-4 inches. Support 23 must generally be of moldable polymers typical of sterilizable and medical use, preferably of the same polymer as adapter 25 and sections 11 and 12. Support 23 and sections 11 and 12 are preferably as thin as possible to minimize polymer used but preferably not thinner than 1 millimeter to preserve structural strength required for the objects of the invention and protection of a user from needle wounds from needle 21. Further, polymers for sections 11 and 12 are preferably clear or somewhat translucent so that an outline of needle 21 or an inserted medical liquids container can be determined with clinic or hospital light shining through sections 11 or 12. Visibility of needle 21 and/or such a medical liquids container can be achieved through slots 28 quite easily, but clear or translucent sections 11 and 12 provide additional visualization of those structures.

Figure 2:
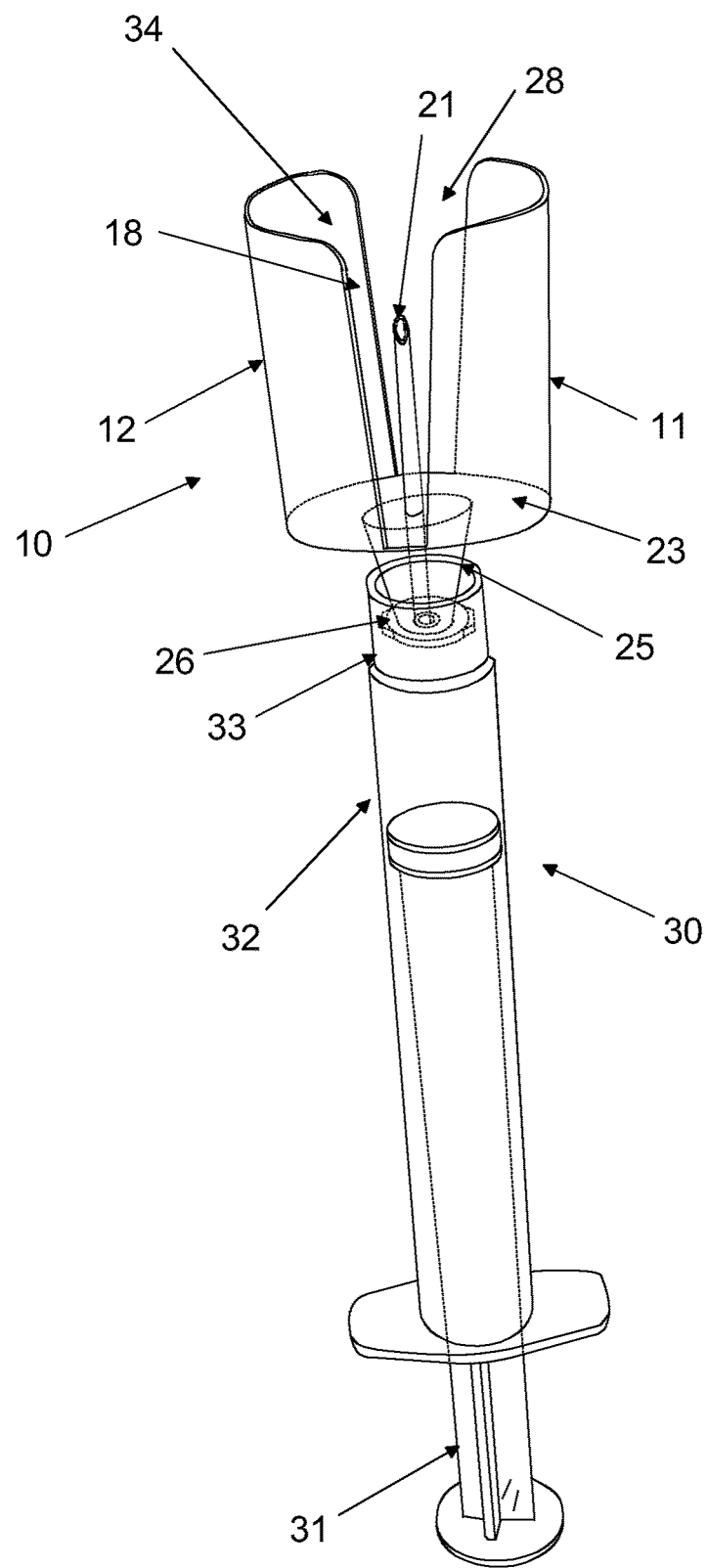
FIG. 2 shows the deflectable guide of FIG. 1 fixed to a syringe and ready for use with a medical liquid container.

FIG. 2 shows syringe 30 (with Luer lock tip 33, plunger 31 and barrel 32) connected by adapter 25 at connector 26 with a tip of syringe 30, resulting in aligned orientation of needle 21, barrel 32, and sections 11 and 12. Needle 21 is clearly visible through slots 28 as being axially aligned within a downward cylindrical space 34 between sections 11 and 12. The tip of needle 21 is always within space 34 and preferably shorter than sections 11 and 12 by at least about one half the diameter of support 23, whereby inward deflection of sections 11 and 12 without a solid object therein will still protect a user's hand from harm.

In approaching a design of a deflectable guide according to one form of the invention, the needle is made only long enough to pierce an intended septum thickness to provide fluid access to a medical container. Minimizing needle length accordingly reduces vertical length of arcuate sections needed for guidance of the needle and user protection.

Figure 3:
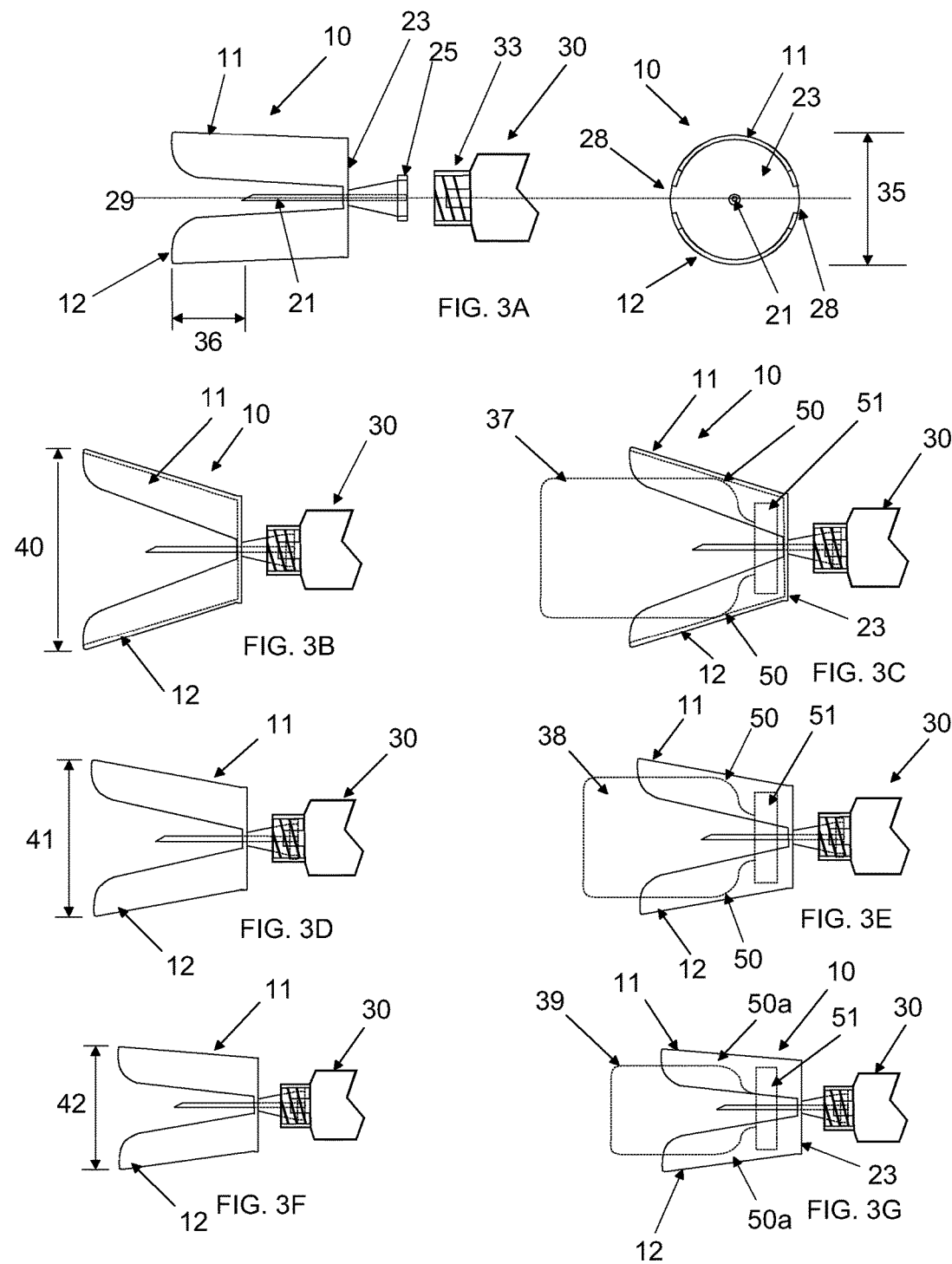
FIG. 3A is a side view of the deflectable guide with an operating axis aligning it with a bottom view of the deflectable guide.
FIGS. 3B and 3C are side views for the deflectable guide of FIG. 3A showing outward deflection of arcuate sections respectively without and with the presence of a large size cylindrical medical liquid container (shown in broken lines).
FIGS. 3D and 3E are side views for the deflectable guide of FIG. 3A showing outward deflection of arcuate sections respectively without and with the presence of a medium size cylindrical medical liquid container (shown in broken lines).
FIGS. 3F and 3G are side views for the deflectable guide of FIG. 3A a lack of or inward deflection of arcuate sections respectively without and with the presence of a small size cylindrical medical liquid container (shown in broken lines).

FIG. 3A is a side view of the deflectable guide 10 with an operating axis 29 aligning it with an axis of syringe 30 and bottom view of the deflectable guide 10 to show certain dimensions and orientations of the features. Distance 36 between lower ends of sections 11 and 12 and the tip of needle 21 shows that sections 11 and 12 will protectably collapse upon the tip of needle 21 on inward deflection of sections 11 and 12 if a user inadvertently grasps guide 10 without engaging it to a medical liquids container. While a medical liquids container is engaged with guide 10 as in FIGS. 3C, 3E and 3G, it will be appreciated from inspection of the bottom view in FIG. 3A that a user's hand never comes closer to needle 21 than about half the diameter 35 and that the guiding effect of sections 11 and 12 inevitably result in needle 21 being guided into impression and piercing the septum of the engaged medical liquids container.

It is an object of the invention that the relative vertical lengths of the arcuate sections, slots between them, needle length, and effective inside diameter of cylindrical space defined within the arcuate sections be chosen with reference to these specific examples as a general guide, not as a specific limitation excepting to achieve the objects of the invention to protect a user from needle wounds.

FIGS. 3B and 3C are side views for the deflectable guide 10 of FIG. 3A showing outward deflection 40 of arcuate sections 11 and 12 respectively without and with the presence of a large size cylindrical medical liquid container 37 (shown in broken lines). Shoulder contacts 50 are shown for FIGS. 3C and 3E between respectively medical liquid containers 37 and 38, resulting respectively in lower end deflections of 40 and 41 in FIGS. 3B and 3D. Septum caps 51 are shown identical for all the medical liquid containers in FIGS. 3C, 3E, and 3G but can be variable depending on the container. Referring to FIGS. 3B and 3C, inside surfaces of sections 11 and 12 are shown in broken lines to indicate contact surfaces for medical liquid containers. A user's hand grasps the outside surfaces of deflected sections 11 and 12, causing a frictional embrace and direction guiding effect for the engaged medical liquid containers.

FIGS. 3F and 3G are side views for the deflectable guide 10 of FIG. 3A a lack of or inward deflection of arcuate sections 11 and 12 respectively without and with the presence of a small size cylindrical medical liquid container 39 (shown in broken lines) resulting in no or inward deflection 42. If an outer diameter of container 39 is less than support 23, sections 11 and 12 will inwardly deflect, with lower ends of sections 11 and 12 forming an embracing and frictional engagement to guide container 39 appropriately toward a septum of container 39.

Figure 4:
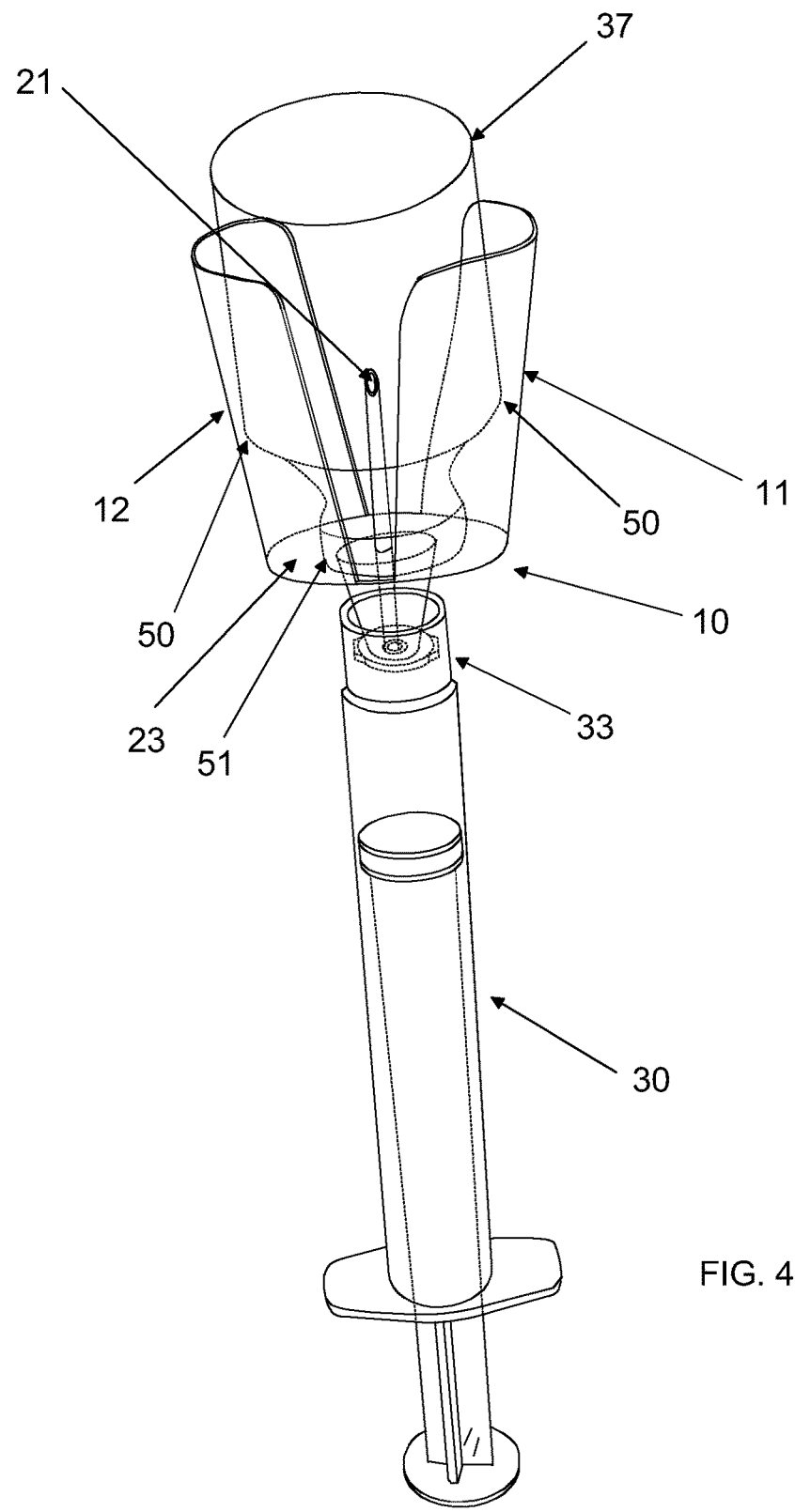
FIG. 4 is a top perspective view of the combination of a syringe and deflectable guide of FIG. 2 showing deflection of arcuate sections as in FIG. 3C or 3E.

FIG. 4 is the combination of a syringe 30 and deflectable guide 10 of FIG. 2 showing deflection of arcuate sections 11 and 12 as in FIG. 3C or 3E.

Figure 5:
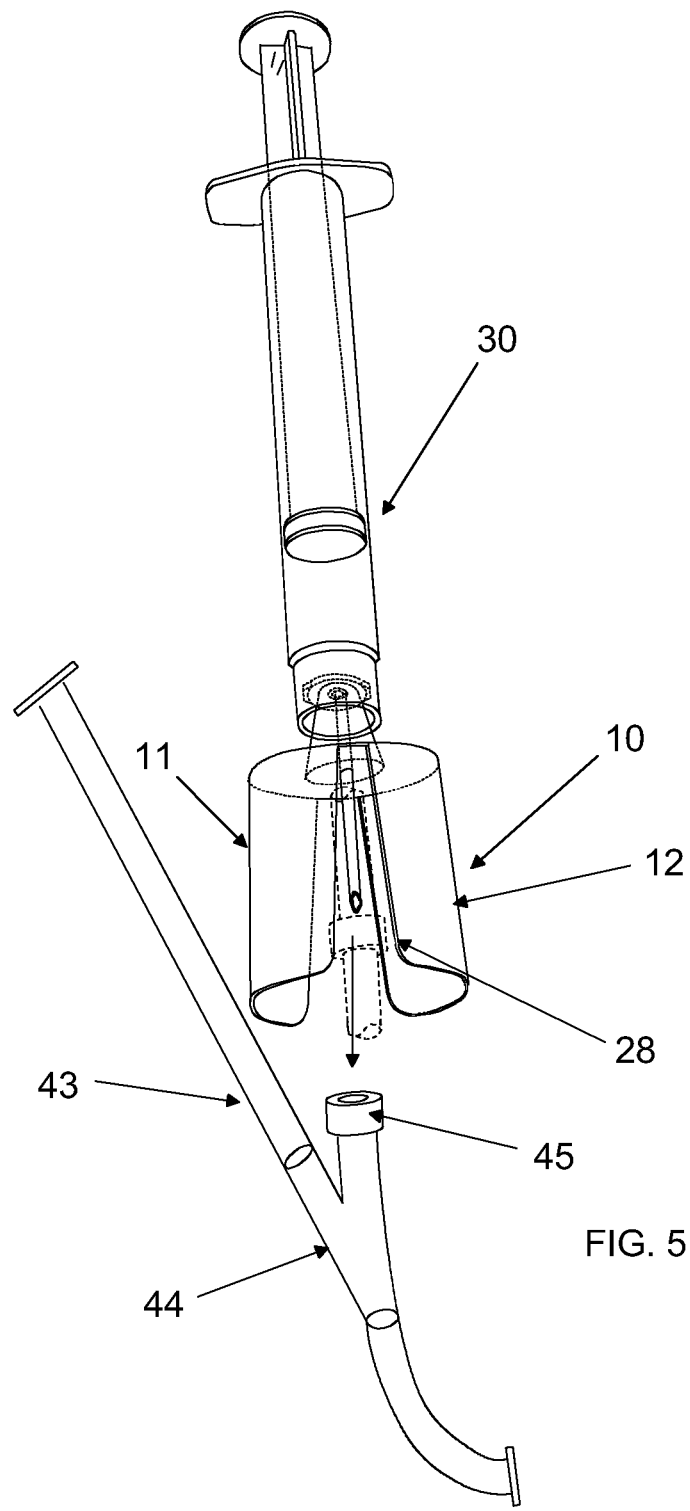
FIG. 5 is the combination of a syringe and deflectable guide of FIG. 2 showing use for injection of medical liquids into an intravenous tubing septum.

FIG. 5 is the combination of a syringe 30 and deflectable guide 10 of FIG. 2 showing use for injection of medical liquids into an intravenous tubing septum 45 fixed with Y-connector 44 and intravenous tubing 43. The combination of a syringe 30 and deflectable guide 10 is rotated left or right so that slots 28 allow for passage of tubing 43 through them to allow septum 45 to engage with needle 21. Further, connector 44 and tubing 43 are shown in broken lines in FIG. 5 aligned so that a continuous portion of tubing 43 passes through a slot of guide 10 while septum 45 is aligned to be pierced by needle 21.

Figure 6:
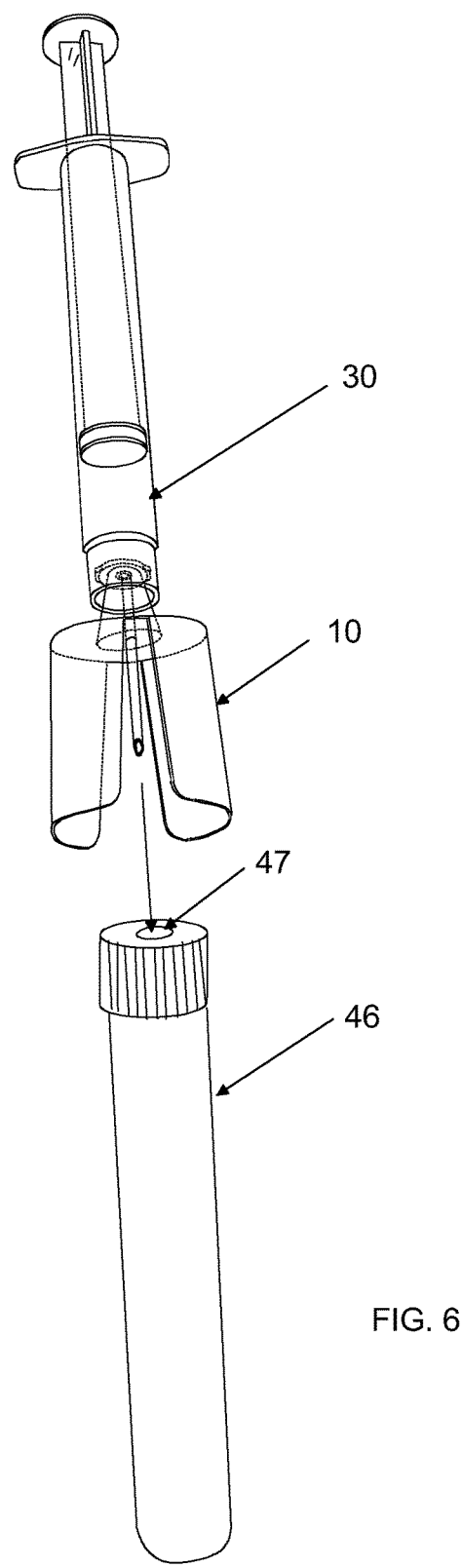
FIG. 6 is the combination of a syringe and deflectable guide of FIG. 2 showing use for injection of medical liquids into specimen tube with a rubber septum.

FIG. 6 is the combination of a syringe 30 and deflectable guide 10 of FIG. 2 showing use for injection of medical liquids into specimen tube 46 with a rubber septum 47.

In general, the invention medication drawing system consists of a plastic winged enclosure surrounding a metal needle. The enclosure serves to guide and center a medication vial into the needle and to guard the needle tip so as to prevent accidental needle stick injury. The invention deflectable guide attaches to either Luer lock or Luer slip syringes that are used to draw the medication from a vial. The invention deflectable guide flanges are made of flexible plastic with a memory, allowing two semicircular flanges to flare out and then spring back to an original orientation. This deformation allows vials of different size and diameter to be inserted into the invention deflectable guide for medication drawing. Thus, a one-size invention deflectable guide will fit all medication vials. When a small vial is inserted into the invention deflectable guide, the flanges center the vial onto the metal needle, after which the medication is withdrawn. When larger vials are inserted, the vial expands the flexible flanges outward, thus accommodating the vial's larger diameter. As with smaller vials, the invention deflectable guide centers the vial onto the needle for easy and efficient medication withdrawal.

The invention deflectable guide needle is in one form shorter than a typical needle used to draw medications so that it does not protrude past the protective flanges and its tip remains within the inverted vial's neck upon use to ensure withdrawal of the entire liquid volume.

The invention deflectable guide's flanges extend beyond the length of the metal needle, such that it is nearly impossible to accidentally stick the needle into the hand that is holding the medication vial. The flanges guide and center the vial's rubber stopper to the needle, reducing accidental needle sticks. Even if the practitioner were to totally miss the vial when trying to insert the needle, the plastic flanges would guard the needle and thus prevent a needle stick.

During medication withdrawal with a standard needle there are two maneuvers that place the user at great risk of needle stick: 1) needle insertion into the vial's stopper, and 2) needle recapping. The insertion maneuver requires a long needle, usually 1.25 to 2.0 inches, to be inserted into the center of the vial's rubber stopper. Given that the needle is at the end of a syringe and the vial is held in the other hand, the maneuver requires hand eye coordination to puncture the center of the rubber stopper. Any lapse in concentration, loss of focus or balance, or external interference (such as another worker accidentally bumping one's hand) can lead to a needle stick of the hand that is holding the vial. In the operating room, where medications are drawn in close proximity to the patient and while wearing gloves, such punctures can introduce pathogens into the provider, as well as contaminate the patient with the provider's blood. Such activity can lead to transmission of blood borne pathogens such as HIV and Hepatitis, exacting a heavy toll on the individual and the healthcare system as a whole. Once a medication is drawn the needle is removed from the vial; in order to be removed it is recapped for 2 reasons: 1) to cover the sharp tip to prevent needle stick upon needle removal, 2) to facilitate grip of the needle for easier removal, especially from Luer lock syringes. The needle cap is bigger and has ridges, making it much easier to grab and unscrew from the syringe than an exposed needle. Unfortunately, the act of re-capping the needle is a dangerous one, often itself leading to the needle stick. It is for this reason that OSHA has mandated all providers to never recap needles using two hands, given the high needle stick risk of this maneuver.

The invention deflectable guide eliminates both of these sources of needle stick. The device's design centers the vial onto the needle, thus dramatically reducing the hand eye coordination needed to align the needle to the rubber stopper. However, should a misalignment occur regardless, the protective flange would impact the hand rather than the short guarded needle, thus preventing needle-stick. Furthermore, given the invention deflectable guide's physical size and design, which incorporates ridges to improve hand grip, removal from the syringe is simple, easy, and does not require needle recapping, thus removing this dangerous step and reducing needle-stick risk. One simply needs to grab the invention deflectable guide in one hand, the syringe in the other, and simply unscrew the invention deflectable guide from the syringe.

Sometimes providers need to inject the medication into rubber I.V. tubing ports during medical care. Such a maneuver is a high risk for needle-stick when performed with a sharp needle, again because any misalignment can cause the provider to miss the port and instead puncture one's hand. The invention deflectable guide can be used in such scenarios to prevent needle-stick, as it can connect to and puncture the I.V. port. The I.V. tubing and plastic port is simply inserted into the space between the flanges, allowing the needle to puncture the rubber port and access the patient.

Finally, there are times when practitioners are asked to draw blood samples from intra-arterial and intravenous catheters. These samples are drawn via syringes that are attached to the catheters or tubing lines that are connected to them; the blood is then transferred to the specimen tube, which is sent to the laboratory. Usually a needle is used to puncture the specimen tube to inject the blood from the syringe. This maneuver poses a very high risk of needle stick. Alternatively, some practitioners remove the rubber cap of the specimen tube to allow its filling without the use of a needle. However, this step has two drawbacks: 1) the vacuum is lost such that the cap can easily fall of during transport, with subsequent loss of the specimen, 2) the tube can be over or under filled as there is no vacuum to draw in the correct volume. The invention deflectable guide solves this problem by allowing safe injection of blood drawn from syringes into specimen tubes. Once the syringe is filled, the invention deflectable guide is attached; the blood can now be safely injected into the specimen tube via the invention deflectable guide guarded needle. The invention deflectable guide centers the specimen tube on the guarded needle while at the same time protecting the user from needlestick.

Figure 7A:
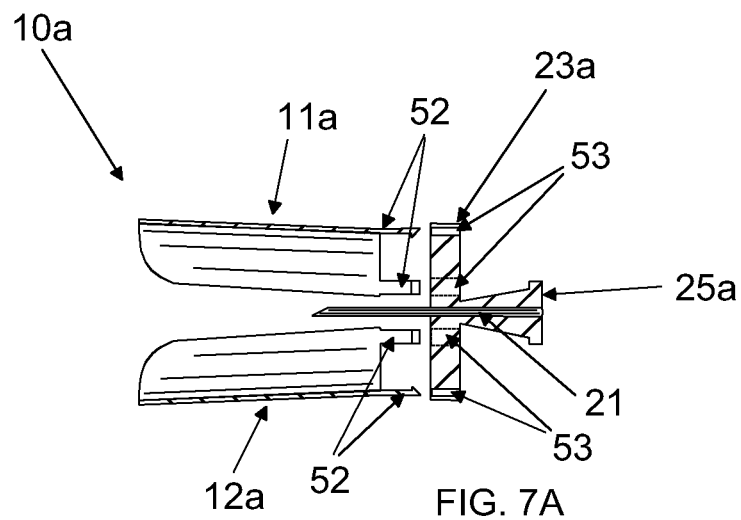
FIG. 7A is a side view of an operating axis cross section of another form of the deflectable guide similar to that of FIG. 3A but having arcuate sections separate but insertable into a radial spacer support.
Figure 7B:
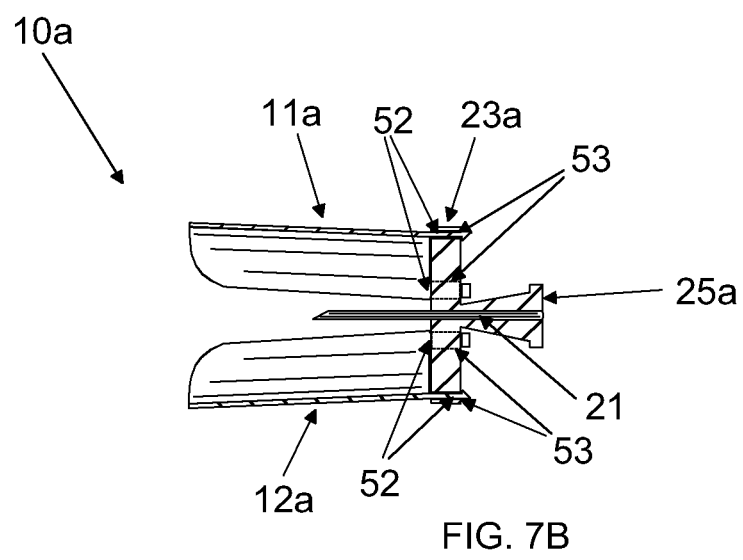
FIG. 7B is a side view of an operating axis cross section of another form of the deflectable guide as in FIG. 7A with its arcuate sections securely inserted into a radial spacer support.

FIG. 7A is a side view of an operating axis cross section of another form of the deflectable guide 10a similar to that of FIG. 3A but having arcuate sections 11a and 12a separate but insertable into a radial spacer support 23a. Notched extensions 52 extend upward from a top edges of sections 11a and 12a. Extensions 52 comprise straight pieces having a sharp inward ledge at a distal end, which are adapted to be inserted into square holes 53 defined in spacer support 23a until the ledges of extensions 52 emerge on a top side of spacer support 23a, as shown in FIG. 7B. Sections 11a and 11b in this form of the invention can be provided separately from the integral adapter 25a and spacer support 23a and attached to support 23a at or near the time that the invention assembly is used.

FIG. 7B is a side view of an operating axis cross section of another form of the deflectable guide as in FIG. 7A with its arcuate sections securely inserted into a radial spacer support.

The above design options will sometimes present the skilled designer with considerable and wide ranges from which to choose appropriate apparatus and method modifications for the above examples. However, the objects of the present invention will still be obtained by that skilled designer applying such design options in an appropriate manner.

I claim:

1. An assembly of a syringe rigidly engaged at a syringe tip to a deflectable guide comprising:
   (a) the deflectable guide comprising a hypodermic needle secured in a center of a round spacer support that extends radially and normally outward from an operating axis defined by a bore of the hypodermic needle and at an upper end of the hypodermic needle, wherefrom an integral adapter extends up from a top surface of the round spacer support adapted to be rigidly engaged or disengaged with a Luer lock, slip lock or other tip of the syringe;
   (b) two arcuate sections are supported in a downward direction from a periphery of the round spacer support, the arcuate sections having inside surfaces defining a cylindrical or frustro-conical protected space and sharing the operating axis where a free portion of the needle extends down from the round spacer support to the needle tip, which is always within the protected space;
   (c) the arcuate sections are returnably flexible at their connections at upper ends to the round spacer support:
      (i) so that lower ends of the arcuate sections deflect outward and away from the operating axis when the arcuate sections engage a container whose engaged diameter is greater than that of the round spacer support; and
   (d) the arcuate sections are optionally removable or engageable at upper edges to a bottom periphery of the round spacer support.

2. The assembly of claim 1 wherein the arcuate sections are greater in operating axis length than the free portion of the needle by a distance of equal to or greater than one half of an inside diameter of the spacer support.

3. The assembly of claim 1 wherein the spacer support is integral with the adapter.

4. The assembly of claim 1 wherein the spacer support is separable from the adapter.

5. The assembly of claim 1 wherein there are only two arcuate sections which are separated at adjacent edges by slots.

6. The assembly of claim 5 wherein the slots are adapted to provide visualization of the needle by a user viewing the deflectable guide in a side view.

7. The assembly of claim 6 wherein the inside surfaces of the arcuate sections are adapted to slidably engage a top section of a medical liquid container having an outside cylindrical diameter greater than an inside diameter of the spacer support.

8. The assembly of claim 7 wherein the arcuate sections are adapted to deflect outward from their lower ends upon engaging the medical liquid container having an outside cylindrical diameter greater than an inside diameter of the spacer support.

9. The assembly of claim 6 wherein the inside surfaces of the arcuate sections are adapted to slidably engage a middle or lower section of a medical liquid container having an outside cylindrical diameter less than an inside diameter of the spacer support.

10. The assembly of claim 9 wherein the arcuate sections are adapted to deflect inward from their lower ends upon engaging the medical liquid container having an outside cylindrical diameter less than an inside diameter of the spacer support.

11. The assembly of claim 1 wherein the spacer support comprises a polymer disk having an inside diameter of from 0.5 inches to 2.0 inches.

12. The assembly of claim 11 wherein the operating axis length of the arcuate sections is from 0.5 inches to 4.0 inches.

* * * * *